United States Patent
Carano et al.

(10) Patent No.: US 9,409,176 B2
(45) Date of Patent: Aug. 9, 2016

(54) SAMPLE CONTAINER WITH PHYSICAL FILL-LINE INDICATOR

(75) Inventors: Donald J. Carano, North Lawrence, OH (US); Rick Cook, Sparta, NJ (US); Michael Iskra, Bridgewater, NJ (US); C. Mark Newby, Tuxedo, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1105 days.

(21) Appl. No.: 11/851,965

(22) Filed: Sep. 7, 2007

(65) Prior Publication Data

US 2008/0125673 A1   May 29, 2008

Related U.S. Application Data

(60) Provisional application No. 60/843,160, filed on Sep. 8, 2006.

(51) Int. Cl.
*B01L 3/00* (2006.01)
*A61B 5/15* (2006.01)
*A61B 5/154* (2006.01)

(52) U.S. Cl.
CPC ............ *B01L 3/5082* (2013.01); *A61B 5/1405* (2013.01); *A61B 5/15003* (2013.01); *A61B 5/1545* (2013.01); *A61B 5/150351* (2013.01); *A61B 5/150755* (2013.01); *B01L 2200/12* (2013.01); *B01L 2300/02* (2013.01); *B01L 2300/044* (2013.01); *B01L 2300/0854* (2013.01); *Y10T 29/4998* (2015.01); *Y10T 29/49879* (2015.01)

(58) Field of Classification Search
CPC . A61B 5/1405; B01L 3/5082; B01L 2200/12; B01L 2300/044; B01L 2300/02; B01L 2300/0854; Y10T 29/4998; Y10T 29/49879
USPC .................................................. 600/573–583
See application file for complete search history.

(56) References Cited

U.S. PATENT DOCUMENTS

| 2,528,259 | A |   | 10/1950 | Annunziata |
|-----------|---|---|---------|-----------|
| 3,800,780 | A |   | 4/1974  | Elliott |
| 3,807,955 | A | * | 4/1974  | Note et al. ..................... 436/177 |
| 3,942,514 | A |   | 3/1976  | Ogle |

(Continued)

FOREIGN PATENT DOCUMENTS

| CA | 2496713 | 4/2004 |
|----|---------|--------|
| DE | 102004009419 | 11/2004 |

(Continued)

OTHER PUBLICATIONS

H. Rees, "Mold Engineering", 2nd Edition, p. 108, Beijing Chemical Industry Press, Jan. 2005.

*Primary Examiner* — Rene Towa
(74) *Attorney, Agent, or Firm* — The Webb Law Firm

(57) ABSTRACT

A collection container for collecting biological fluid specimens having an integral fill-line indicator which corresponds to a desired specimen volume is disclosed. The integral fill-line indicator may comprise a ridge that is raised from the surface of the collection container. The integral fill-line indicator may also be altered by surface modification to impart a distinct visual appearance and/or texture. The collection container may have a single or a plurality of integral fill-line indicators which correspond to a desired specimen volume range. A method of manufacturing a collection container having an integral fill-line indicator is also disclosed.

19 Claims, 14 Drawing Sheets

(56) References Cited

U.S. PATENT DOCUMENTS

| | | | |
|---|---|---|---|
| 4,015,352 A | 4/1977 | Prange | |
| 4,109,530 A | 8/1978 | Kim | |
| 4,125,376 A | 11/1978 | Razulis | |
| 4,344,994 A | 8/1982 | Batty et al. | |
| 4,391,780 A | 7/1983 | Boris | |
| 4,475,915 A | 10/1984 | Sloane | |
| 4,557,070 A * | 12/1985 | Oyama | 47/80 |
| 4,761,379 A | 8/1988 | Williams et al. | |
| 4,805,635 A | 2/1989 | Korf et al. | |
| 4,827,944 A | 5/1989 | Nugent | |
| 4,830,217 A | 5/1989 | Dufresne et al. | |
| 4,871,077 A | 10/1989 | Ogden et al. | |
| 4,873,193 A | 10/1989 | Jensen et al. | |
| 4,877,585 A | 10/1989 | Perlman | |
| 4,878,597 A * | 11/1989 | Haast | 34/108 |
| 4,942,966 A | 7/1990 | Kemp | |
| 4,981,144 A * | 1/1991 | Carels, Jr. | 600/573 |
| 5,019,243 A | 5/1991 | McEwen et al. | |
| 5,024,238 A | 6/1991 | Guirguis | |
| 5,048,711 A | 9/1991 | Weiss et al. | |
| 5,059,185 A | 10/1991 | Ryan | |
| 5,061,263 A | 10/1991 | Yamazaki et al. | |
| 5,071,168 A | 12/1991 | Shamos | |
| 5,164,575 A | 11/1992 | Neeley et al. | |
| 5,178,417 A | 1/1993 | Eshoo | |
| 5,181,523 A | 1/1993 | Wendelborn | |
| 5,215,102 A | 6/1993 | Guirguis | |
| 5,316,952 A | 5/1994 | Brimhall et al. | |
| 5,381,487 A | 1/1995 | Shamos | |
| 5,401,110 A | 3/1995 | Neeley | |
| 5,447,248 A | 9/1995 | Rodriguez et al. | |
| 5,516,564 A | 5/1996 | Root et al. | |
| 5,556,599 A | 9/1996 | Ahmed | |
| 5,725,832 A | 3/1998 | Gundelsheimer | |
| 5,728,267 A | 3/1998 | Flaherty | |
| 5,736,033 A | 4/1998 | Coleman et al. | |
| 5,786,228 A * | 7/1998 | Charlton | 436/177 |
| 5,855,289 A | 1/1999 | Moore | |
| 5,871,700 A * | 2/1999 | Konrad | 422/547 |
| 5,900,291 A | 5/1999 | Pebbles | |
| 5,915,583 A | 6/1999 | Cloonan et al. | |
| 5,924,594 A | 7/1999 | Kelly | |
| 5,928,215 A | 7/1999 | Caizza et al. | |
| 5,961,472 A | 10/1999 | Swendson et al. | |
| 5,981,293 A | 11/1999 | Charlton | |
| 6,062,407 A | 5/2000 | Moore | |
| 6,209,921 B1 | 4/2001 | Hogan et al. | |
| 6,279,759 B1 | 8/2001 | Weisbach | |
| 6,354,452 B1 | 3/2002 | DeSalvo et al. | |
| 6,364,866 B1 | 4/2002 | Furr et al. | |
| 6,428,640 B1 | 8/2002 | Stevens et al. | |
| 6,439,276 B1 | 8/2002 | Wood et al. | |
| 6,497,325 B1 | 12/2002 | DiCesare et al. | |
| 6,540,697 B2 | 4/2003 | Chen | |
| 6,555,386 B1 | 4/2003 | Rees | |
| 6,588,681 B2 | 7/2003 | Rothrum et al. | |
| 6,599,481 B2 | 7/2003 | Stevens et al. | |
| 6,612,997 B1 * | 9/2003 | Hutton | 600/573 |
| 6,613,410 B1 | 9/2003 | Sellars | |
| 6,651,835 B2 | 11/2003 | Iskra | |
| 6,663,018 B2 | 12/2003 | Rothrum et al. | |
| 6,716,192 B1 | 4/2004 | Orosz, Jr. | |
| 6,749,078 B2 | 6/2004 | Iskra | |
| 6,770,244 B2 | 8/2004 | Hool et al. | |
| 6,793,075 B1 | 9/2004 | Jeter | |
| 6,910,597 B2 | 6/2005 | Iskra | |
| 6,946,100 B2 | 9/2005 | Yokoi et al. | |
| 7,122,157 B2 | 10/2006 | Stevens et al. | |
| 2002/0011492 A1 * | 1/2002 | Iskra | 220/23.87 |
| 2002/0183651 A1 | 12/2002 | Hyun | |
| 2003/0059347 A1 * | 3/2003 | Ostgaard et al. | 422/102 |
| 2003/0070338 A1 | 4/2003 | Roshkoff | |
| 2003/0145945 A1 | 8/2003 | Kennedy | |
| 2004/0025603 A1 | 2/2004 | Liseo et al. | |
| 2004/0025935 A1 | 2/2004 | Liseo et al. | |
| 2004/0079753 A1 | 4/2004 | Reichenbach et al. | |
| 2004/0091401 A1 | 5/2004 | Golabek et al. | |
| 2004/0222223 A1 | 11/2004 | Swenson | |
| 2004/0223889 A1 | 11/2004 | Reichenbach | |
| 2005/0109794 A1 | 5/2005 | Murakami et al. | |
| 2006/0091669 A1 | 5/2006 | Wilkinson | |
| 2006/0099112 A1 | 5/2006 | Fitz | |
| 2006/0133963 A1 | 6/2006 | Stein et al. | |
| 2006/0233675 A1 | 10/2006 | Stein | |
| 2006/0233676 A1 | 10/2006 | Stein | |
| 2006/0255235 A1 * | 11/2006 | Meyer et al. | 249/140 |

FOREIGN PATENT DOCUMENTS

| | | |
|---|---|---|
| DE | 102004005381 | 12/2004 |
| DE | 102004014845 | 10/2005 |
| EP | 1199104 A2 | 4/2002 |
| EP | 1539598 | 6/2005 |
| EP | 1285694 | 2/2006 |
| GB | 1425964 | 2/1976 |
| JP | 62110139 | 7/1987 |
| JP | 63188768 | 8/1988 |
| JP | 2-82312 | 6/1990 |
| JP | 11301696 A | 11/1999 |
| JP | 2002148152 | 5/2002 |
| JP | 2003004605 | 1/2003 |
| JP | 2003153884 | 5/2003 |
| WO | 01/54816 A | 8/2001 |
| WO | 2004018304 A2 | 8/2003 |
| WO | 2004018304 | 3/2004 |
| WO | 2004022234 | 3/2004 |
| WO | 2004043601 A1 | 5/2004 |
| WO | 2006050319 A2 | 5/2006 |

\* cited by examiner

SAMPLE CONTAINER WITH PHYSICAL FILL-LINE INDICATOR

The present application claims priority to provisional application No. 60/843,160 filed on Sep. 8, 2006.

BACKGROUND OF THE INVENTION

1. Field of the Invention

The present invention relates to a biological sample container and, more particularly, to a biological fluid collection container having at least one fill-line indicator.

2. Description of Related Art

Biological sample containers have historically been used for the collection of specimens, such as blood and other bodily fluids, for the purpose of, for example, performing diagnostic tests. In many cases, a predetermined volume of specimen is required to perform a specific test, and such containers are often utilized to facilitate collection of a precise test-specific specimen volume, for example, with a fluid collection container such as a blood collection tube. In some such sample containers, a pre-measured additive, such as a preservative or anticoagulant, is deposited into the container to preserve or otherwise prepare the sample. Accordingly, it is important that the amount of fluid sample collected within the container correspond to the volume of additive within the container and/or the desired test volume.

Traditional methods of measuring specimen volume have included placing an adhesive label on the exterior surface of the sample container at a precise location. This allows medical personnel to measure the specimen volume by aligning the amount of liquid within the container with a designation on the label, or the upper or lower edge of the label. This method, however, can have significant drawbacks. Complicated machinery is necessary to properly align the label on the exterior of the sample container. Errors in label placement can cause inaccurate fill volumes and consequently inaccurate corresponding test results, especially where sample to additive ratios are to be properly managed and maintained. Sample containers having misaligned labels are typically discarded as defective products and contribute to increased costs. In addition, labels affixed to the exterior of a sample container can become damaged through routine procedures, and can be easily covered over by additional patient or sample collection indicia.

SUMMARY OF THE INVENTION

Consequently, there is a need for an improved sample container that allows medical personnel to visually obtain a precise volume of specimen and/or a combined expected volume of specimen with a reagent present in the container.

According to an aspect of the present invention, a specimen collection container assembly comprises a first opening, a first closed bottom, and a first sidewall extending circumferentially between the first opening and the first closed bottom. This first tubular member is capable of receiving a specimen sample therein. The container assembly further comprises a second tubular container having a second opening, a second closed bottom, and a second sidewall extending circumferentially between the second opening and the second closed bottom. The first tubular member is disposed within the second tubular member. A fill-line indicator is positioned on one of the first and second sidewall. This fill-line indicator corresponds to at least a minimum expected fill volume of the collection container.

According to another aspect of the present invention, a biological specimen collection container assembly comprises a first tubular member having a first opening, a first closed bottom, and a first sidewall extending circumferentially between the first opening and the first closed bottom. This first tubular member is capable of receiving a specimen sample therein. The container assembly further comprises a second tubular member having a second opening, a second closed bottom, and a second sidewall extending circumferentially between the second opening and the second closed bottom. This second sidewall has an inner and outer surface and a fill-line indicator integral with an inner surface of the second sidewall. The fill-line indicator corresponds to at least a minimum expected fill volume of the collection container and the first tubular member is disposed within the second tubular member.

According to another aspect of the present invention, the specimen collection container assembly comprises a tubular member having an opening, a closed bottom, and a sidewall extending circumferentially between the opening and the closed bottom. The tubular member is capable of receiving a specimen sample therein. A fill-line indicator is positioned on an inner surface of the sidewall. The fill-line indicator corresponds to at least a minimum expected fill volume of the collection container.

According to yet another aspect of the present invention, a method of making a specimen collection container comprises molding a first tubular member having a first opening, a first closed bottom, and a first sidewall extending circumferentially between the first opening and the first closed bottom. The first tubular member has a predetermined volume for receiving a specimen sample therein. The method further comprises molding a second tubular member having a second opening, a second closed bottom, and a second sidewall extending circumferentially between the second opening and the second closed bottom, providing a fill-line indicator on one of the first and second sidewall wherein this fill-line indicator corresponds to at least a minimum expected fill volume of the collection container, and positioning the first tubular member within the second tubular member.

According to another aspect of the present invention, a method of making specimen collection container comprises molding a tubular member having a first end, a second end, and a sidewall extending circumferentially between the first end and the second end. The tubular member has a predetermined volume for receiving a specimen sample therein. The second end may be a closed bottom of the tube or it may be an open end to form a double open ended tube. In this embodiment, the two openings may be closed by separate closures. The method further comprises providing a fill-line indicator on an inner surface of the sidewall. This fill-line indicator corresponds to at least a minimum expected fill volume of the collection container.

According to a further aspect of the present invention, the fill-line indicator can comprise a single line extending at least partially circumferentially about a portion of one of the first and second sidewall wherein this single line has a first predetermined width that corresponds to a minimum volume of the expected fill volume of the collection container. Alternatively, according to a another aspect of the present invention, the fill-line indicator can comprise an upper and lower line extending at least partially circumferentially about a portion of one of the first and second sidewall and spaced a predetermined distance form each other and wherein the upper line defines a maximum expected fill volume and the lower line defines a minimum expected fill volume and wherein the spacing between the upper and lower line defines a range of volumes of the expected fill volume of the collection container. According to yet another aspect of the present invention, the fill-line indicator can also comprise a single line extending at least partially circumferentially about a portion of one the first and second sidewall wherein this single line has a second predetermined width defined by an upper boundary and lower boundary. The upper boundary defines a maximum expected fill volume, the lower boundary defines a minimum expected fill volume and the second predetermined width defines a range of volumes of the expected fill volume of the collection container.

The fill-line indicator can comprise a visual indicia applied to the first or second sidewall of the first or second tubular member. Alternatively, the fill-line indicator can be formed integrally with the molding material from which the tubular members are formed, to form a textured surface on the first or second sidewall of the first or second tubular member. This textured surface is capable of diffusing light and/or forming an opaque surface on the container and can be formed on one of the tubes during an injection molding process.

Further details and advantages will be understood from the following description of the preferred embodiments, taken with the accompanying drawings, wherein like reference numerals represent like elements throughout.

DETAILED DESCRIPTION OF THE INVENTION

Figures 1, 2, 3:
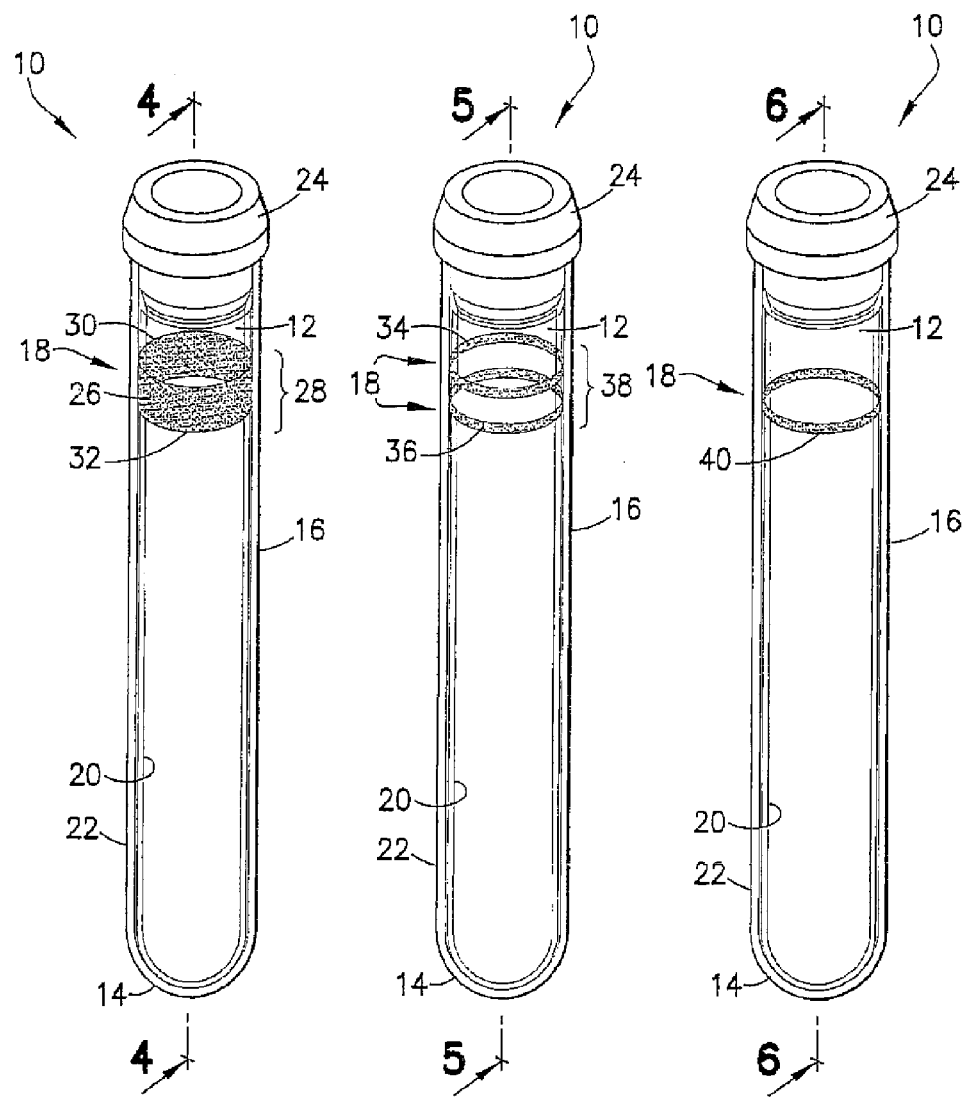
FIG. 1 is a perspective view of a container having a single wide band fill-line indicator according to a first aspect of the invention.
FIG. 2 is a perspective view of a container having a pair of fill-line indicators according to a second aspect of the invention.
FIG. 3 is a perspective view of a container having a single fill-line indicator showing a minimum expected fill volume according to a third aspect of the invention.

For purposes of the description hereinafter, spatial or directional terms shall relate to the invention as it is oriented in the drawing figures. However, it is to be understood that the invention may assume various alternative variations, except where expressly specified to the contrary. It is also to be understood that the specific components illustrated in the attached drawings, and described in the following specification, are simply exemplary embodiments of the invention. Hence, specific dimensions and other physical characteristics related to the embodiments disclosed herein are not to be considered as limiting.

Reference is now made to FIGS. 1-3 which show a perspective view of a collection container, generally indicated as 10, such as a biological fluid specimen collection container. The container 10, comprises a tubular member having an opening 12, a closed bottom 14, and a sidewall 16 extending circumferentially between the opening 12 and the closed bottom 14 to form a tube. The container 10 has a predetermined internal volume capable of receiving a specimen sample therein. A fill-line indicator, generally indicated as 18, is positioned on the sidewall 16. This fill-line indicator 18 corresponds to at least a minimum expected fill volume of the collection container 10. While container 10 is described in certain embodiments herein in the form of a biological fluid collection container such as a blood collection tube, and in particular, an evacuated blood collection tube, it is contemplated that embodiments of the invention can be directed to any biological sample container.

The container 10 of FIGS. 1-3 have an inner surface 20 and an outer surface 22. Blood, urine, and/or other bodily fluids may be collected within the container assembly 10 for subsequent testing procedures. The container 10 may comprise, for example, glass or a polymeric composition, such as polypropylene, nylon, polystyrene, cyclic olefin copolymer polyethylene terapthalate and/or polyethylene. The container may have any suitable length L and any suitable width W (or diameter) consistent with its intended use. In one embodiment, the container 10 represents a collection tube having an expected fill capacity of from about 1 to about 7 milliliters (ml), such as about 2.7 ml. In another embodiment, the container can have an expected fill capacity of about 1.8 ml.

The container 10 comprises a fill-line indicator 18 integrally formed with the sidewall 16 that corresponds to a desired or expected specimen fill capacity. In some embodiments, the desired specimen fill capacity may include only the specimen. In other embodiments, the desired specific fill capacity may include the specimen and the additive. The expected fill volume can be defined as only the volume of the biological fluid, such as blood entering the container or the volume of biological fluid plus an additive such as a reagent. In other cases, the expected fill volume can include the volume of the biological fluid plus a separator (gel or mechanical) and/or the volume of the biological fluid plus a separator and an additive.

The fill-line indicator 18 can indicate at least a desired minimum expected fill volume and can correspond to the meniscus of a liquid specimen contained within container assembly 10. The fill-line indicator 18 can be disposed continuously about the circumference of the sidewall of the container 10 or alternatively, the fill-line indicator 18 can extend at least partially circumferentially about a portion of the sidewall 16.

In embodiments disclosed herein, the fill-line indicator 18 provides the container with an indication as to the expected fill volume for a container 10 when the container 10 is positioned vertically, in this case, upright, i.e., in a closure-up position. In this manner, the fill-line volume indicator 18 provides a confirmation as to whether an amount of sample within the container 10 is the desired or expected fill volume for the container 10. Such a fill-line indicator 18 is particularly helpful for sample collection containers, such as for determining whether the amount of sample within a container matches the particular predetermined draw volume for the specific collection container. In other embodiments, the fill-line volume indicator 18 provides an indication as to the desired or expected fill volume for a container when the container is positioned in a non-vertical position. For example, blood collection containers typically include a negative pressure or vacuum within the interior thereof. A pierceable closure 24 is used to cap the container 10 and maintain this negative pressure therein. In use, a blood collection needle accesses a patient's blood vessel, and is placed in fluid communication with the interior of the blood collection container 10. The negative pressure within the container 10 draws a blood sample from the blood vessel, through the needle and into the interior of the collection container. Eventually, the pressure within the collection container 10 is equilibrated with the blood pressure, at which time no additional sample is drawn into the collection container. Accordingly, the interior of the collection container 10 may include a negative pressure to provide sufficient vacuum within the collection container 10 to ensure that a predetermined volume of blood is drawn into the container based on that vacuum.

Further, sample containers 10 may incorporate specific reagents therein, associated with a desired test to be performed on the sample. One example of a reagent includes a citrate. The amount of reagent may be particularly tailored to the specific expected fill volume of sample for the container. If the amount of sample drawn into the container 10 does not match the specific expected fill volume of the specimen sample and reagent, the reagent may not properly react with the sample, thereby possibly providing inaccurate testing results. The fill-line indicator 18 provides a mechanism to facilitate ensuring that the proper volume of sample for reacting with the reagent in the container is collected within the container 10. For example, long-term storage of evacuated collection containers can result in reduced vacuum therein, thereby reducing the draw volume for the container 10. Moreover, during an initial blood draw, the needle may include air therein which is displaced into the first collection container used in the draw. Such air may decrease the overall fill volume for the container 10, such that an insufficient amount of blood is drawn into the container for the reagent contained therein. By providing the fill-line indicator 18, the user can confirm that the appropriate amount of sample expected for that container 10 has in fact been collected within the container 10 immediately after the blood draw. Moreover, by providing the fill-line indicator 18 integral with the container itself, the expected fill volume is effectively set and is incorporated directly with the container, without the chance of misalignment of a separate label identifying the intended or expected fill volume.

Still further, the fill-line indicator 18 can provide confirmation to a lab technician as to whether the volume contained within a container 10 is the expected fill volume, particularly for a specific type of container. This indication may also be useful for confirming whether a sample has already been removed from the container 10 for analysis.

In one embodiment, the fill-line indicator 18 represents a portion of sidewall 16 that has a different profile, surface, texture, etc., and therefore is adapted to diffuse light passing through the sidewall 16 differently than the remaining portion of sidewall 16 defining container 10.

The fill-line indicator 18 may be formed by a variety of techniques. For example, the fill-line indicator 18 can comprise a ridge that is raised from the sidewall 16 of the assembly, extending circumferentially about the container 10. The ridge can extend from the surface of the sidewall 16. In another embodiment, the ridge can be recessed into the side wall 16 to form a groove. The height of such a ridge and/or the depth of such a groove may be any desired amount, so long as the dimensions of the ridge and/or the groove provide a unique identifier to the human eye (or some other indication) which differentiates the ridge and/or groove from the sidewall 16 to represent the fill-line indicator. In a further embodiment, the fill-line indicator 18 can comprise a colored band that is distinct from the color of the sidewall 16. In such an embodiment, sidewall 16 may be a generally transparent material, with a separate colored band sprayed, stenciled, or otherwise applied to the inner or outer surface of sidewall 16 to form the fill-line indicator 18.

Preferably, the fill-line indicator 18 may be formed during an injection molding process for forming the container 10. In such a process, a mold core member cooperates with a mold cavity and plastic material is injected into the cavity between the core and the cavity to form the tubular member. The fill-line indicator 18 is formed by providing a roughened or textured surface at least partially circumventing a perimeter of the core member. Accordingly, during the molding process, this roughened surface is imparted to the inner surface of the sidewall 16 of the container 10. Providing the roughened or textured surface on the core member, as opposed to the cavity member, of the injection molding device provides the advantage that it is easier to eject the tube off of the core. If a textured or roughened surface were provided in the cavity, such as to provide the fill-line indicator 18 on an outer surface of the sidewall 16, then there is a chance that the tube may become stuck within the cavity. As stated above, it is easier to eject the tube from the core than it is to remove a tube from within a cavity.

In yet another embodiment, the fill-line indicator 18 may comprise a region of the sidewall 16 that has been modified by a surface treatment to impart a distinct visual appearance and/or texture as compared to the remainder of the sidewall 16. In such an embodiment, the region forming fill-line indicator 18 may have a translucent or opaque property, with the remainder of the side wall 16 exhibiting a highly polished transparent appearance. For example, the region of sidewall 16 defining fill-line indicator 22 may be modified by electrical discharge machining, etching, or other similar process to impart a textured appearance as compared to the remainder of the side wall 16. In one embodiment, a portion of side wall 16 intended to define fill-line indicator 18 is roughened to define an array of peaks and valleys. For example, the roughened portion of sidewall may be formed by an electrical discharge machining process so as to form an electrical discharge machining finish. The finished part then is compared visually with a visual standard, such as the Charmilles Technologies Company visual surface standard (Charmilles Technology Company, Lincolnshire, Ill.). Using this standard practice, the roughened surface defines a finish of, for example, 1.6 to 12.5 microns and more preferably, a finish of 4.5 to 12.5 microns. Additionally, the roughened surface may be cross-referenced visually to a Charmilles finish number, such as between 24 and 42, and, more preferably, between 30 and 42. Such a surface provides fill-line indicator 18 with a finish which is distinct from the remainder of sidewall 16, such as a polished surface. Accordingly, the surface defining fill-line indicator 18 diffuses light differently than the remainder of sidewall 16. In this manner, when a liquid sample is contained within container 10, a clear visual indication is observed when the sample is filled to a level at fill-line indicator 18, due to the difference in light diffused through the side wall 16. It is contemplated that certain finishes for fill-line indicator 18 may provide an enlarging effect to the sample when the meniscus of a fluid level is at the fill-line indicator 18, providing an apparent indication of reaching such level of containment.

The thickness or length of the fill-line indicator 18 along sidewall 16 defining the length of container 10 may be any desired length, provided that, in one embodiment, such length represents the suitable range of volume for a specific test when the fluid meniscus of a sample contained within container 10 is aligned therewith.

FIG. 1 shows a fill-line indicator 18 according to a first aspect of the invention wherein this fill-line indicator 18 comprises single wide band or line 26 extending at least partially circumferentially about a portion of the sidewall 16. This single band 26 has a first predetermined width 28 defined by an upper boundary 30 and a lower boundary 32. The upper boundary 30 defines a maximum expected fill volume. The lower boundary 32 defines a minimum expected fill volume. The second predetermined width 28 defines a range of volumes for the expected fill volume of the collection container 10.

FIG. 2 shows a fill-line indicator 18 according to a second aspect of the invention wherein this fill-line indicator 18 comprises an upper line 34 and lower line 36 extending at least partially circumferentially about a portion of the sidewall 16. The upper line 34 and lower line 36 are spaced a predetermined distance 38 from each other. The upper line 34 defines a maximum expected fill volume. The lower line 36 defines a minimum expected fill volume. The predetermined distance 38 between the upper 34 and lower line 36 defines a range of volume of the expected fill volume of the collection container 10.

FIG. 3 shows a fill-line indicator 18 according to a third aspect of the invention wherein this fill-line indicator 18 comprises a single thin line 40 extending at least partially circumferentially about a portion of the sidewall 16. This single line 40 has a second predetermined width 42 corresponding to a minimum volume of the expected fill volume of the collection container.

As noted above, specific reagents may be included within container 10. Fill-line indicator 18 may therefore be associated with a specific volume of sample contained within the container to properly react with such a reagent. Accordingly, in embodiments of the invention, container 10 may include an additive, such as sodium citrate, tri-potassium ethylenediamine tetra-acetate ($K_3$ EDTA), lithium heparin, or the like, which may be added into container 10 in a liquid format, a spray-dried format, or some other format.

As shown in FIGS. 4-12, the container assembly 10 can comprise a dual tube-in-tube configuration. This type of configuration comprises a first tubular member 44 having a first opening 46, a first closed bottom 48, and a first sidewall 49 extending circumferentially between the first opening 46 and the first closed bottom 48. The first tubular member 44 is capable of receiving a specimen sample therein. The container further comprises a second tubular member 52 having a second opening 54, a second closed bottom 56, and a second sidewall 57 extending circumferentially between the second opening 54 and the second closed bottom 56. The first tubular member 44 is disposed within the second tubular member 52. A fill-line indicator 18 is positioned on one of the first and second sidewall. This fill-line indicator 18 corresponds to at least a minimum expected fill volume of the collection container 10. The first tubular member 44 or the inner tube 42, in this instance, has an axial length that is less than the second tubular member 52 or outer tube. As a result, a closure 24 can be inserted into the tops of the container assembly for secure sealing engagement with portions of both the first and second tubular members 44, 52. The outer surface 51 of the first tubular member 44 and the inner surface 58 of the second tubular member 52 may be dimensioned to substantially nest with one another and may be structured in a manner to prevent foreign matter (such as biological sample) from entering any space that may exist between the inner surface 58 of the second tubular member 52 and the outer surface 51 of the first tubular member 44. Such a tube-in-tube configuration is described in detail in U.S. Pat. No. 6,910,597 to Iskra, the entirety of which is incorporated herein by reference thereto.

In a tube-in-tube configuration, differing materials may be used for each of the tubes, for example, one tube may comprise glass and another tube may comprise a polymeric composition to provide improved liquid and vapor resistance. Alternatively, both tubes may be formed from a polymeric composition wherein one of the nested containers may be formed from a material that, for example, exhibits desirable gas barrier characteristics, and the other of the containers may be formed from a material that, for example, provides a moisture barrier. The inner container is formed from a material that has a proper surface for the specified clinical performance of the material being stored in the container assembly. Materials exhibiting desirable gas barrier characteristics include: acrylic polymers and copolymers, including acrylonitrile-butadiene-styrene (ABS), styrene-acrylonitrile (SAN); ethylene vinyl alcohol (EVA); polyesters; polyethylene terephthalate (PET); polyethylene terephthalate glycol (PETG); polyethylene terephthalate naphthalene (PETN); polyethylene naphthalene (PEN); and engineered thermoplastics, including polycarbonate and blends thereof. Materials that exhibit desirable moisture or vapor barrier characteristics include: polyolefins, including polyethylene, polypropylene and copolymers thereof, cyclic olefin copolymers and chloro- and fluoro-polymers, including polyvinylidene chloride (PVDC), polyvinylidene fluoride (PVDF), polyvinyl fluoride (PVF), and chlorotrifluoroethylene (CTFE or ACLAR). In one embodiment, the inner or first tubular member 44 is formed from polypropylene (PP), and the outer or second tubular member 52 is formed from PET.

The first and second tubular members 44, 52 may be fabricated separately such as by an injection molding technique, as discussed in detail above, and subsequently joined. Alternatively, the tubular members can be dually extruded.

Figure 4:
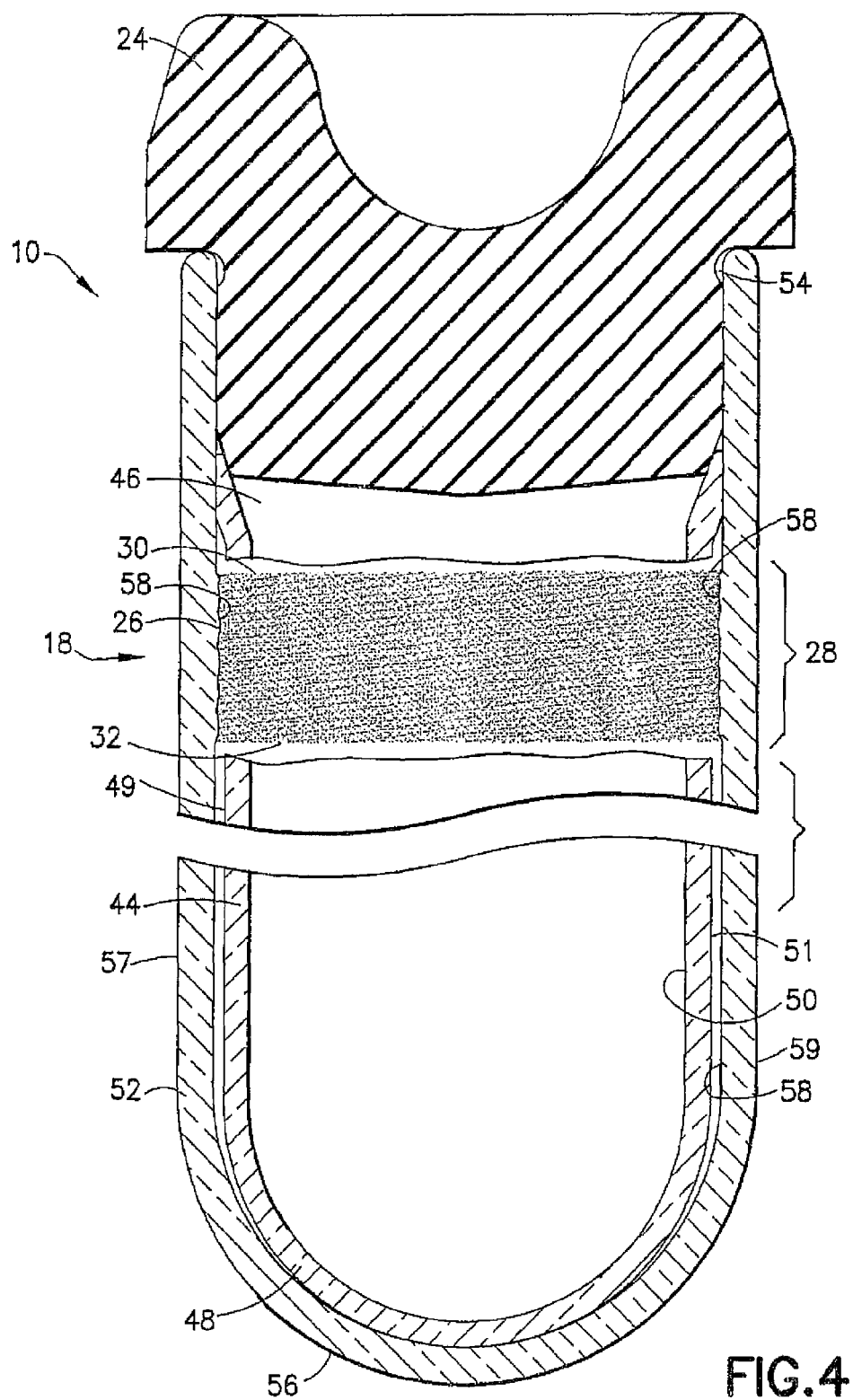
FIG. 4 shows a cross-sectional view of the wide band fill-line of FIG. 1 formed on an inner surface of a second tube according to a first embodiment of the invention.
Figure 5:
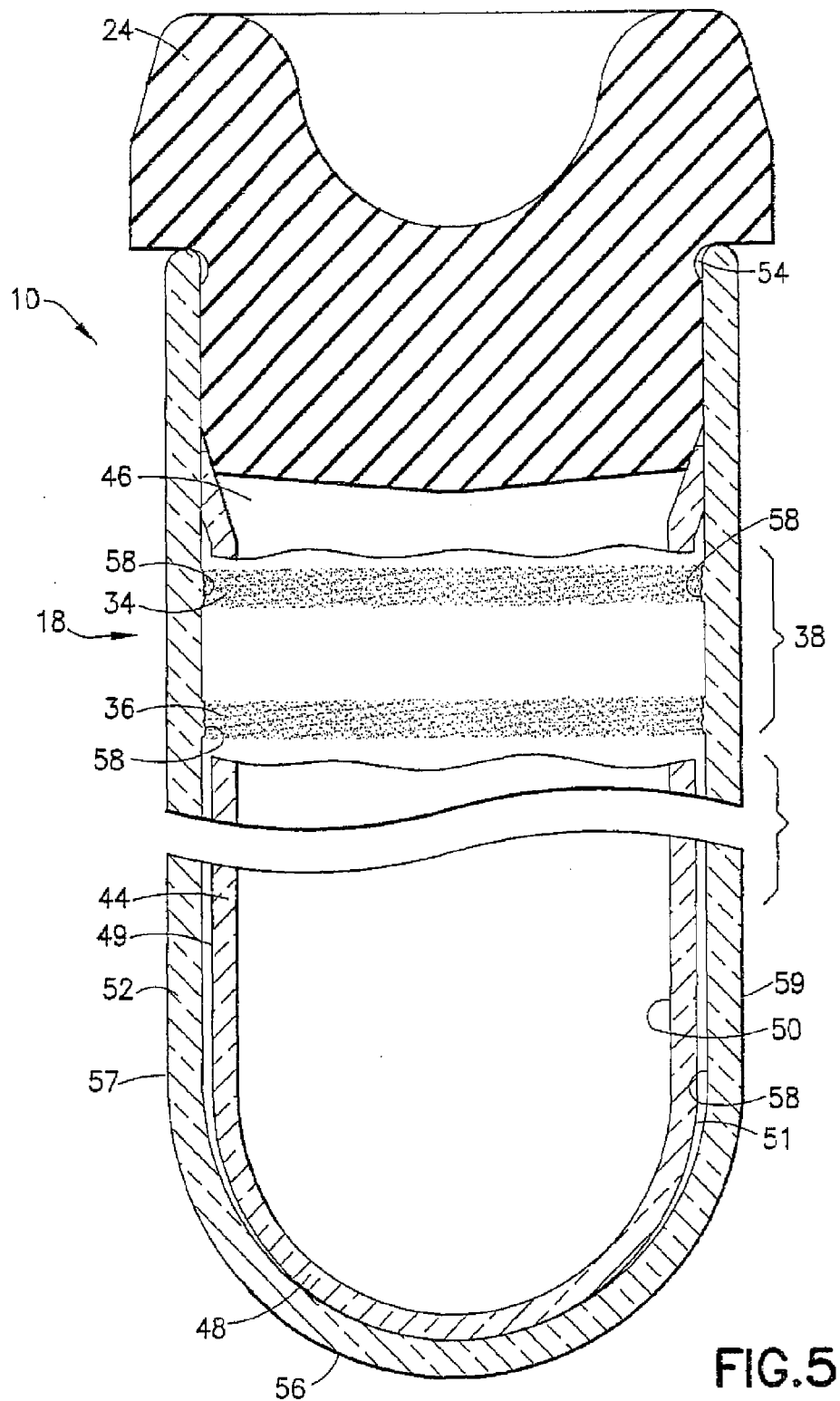
FIG. 5 shows a cross-sectional view of the pair of fill-line indicators of FIG. 2 formed on an inner surface of a second tube according to the first embodiment of the invention.
Figure 6:
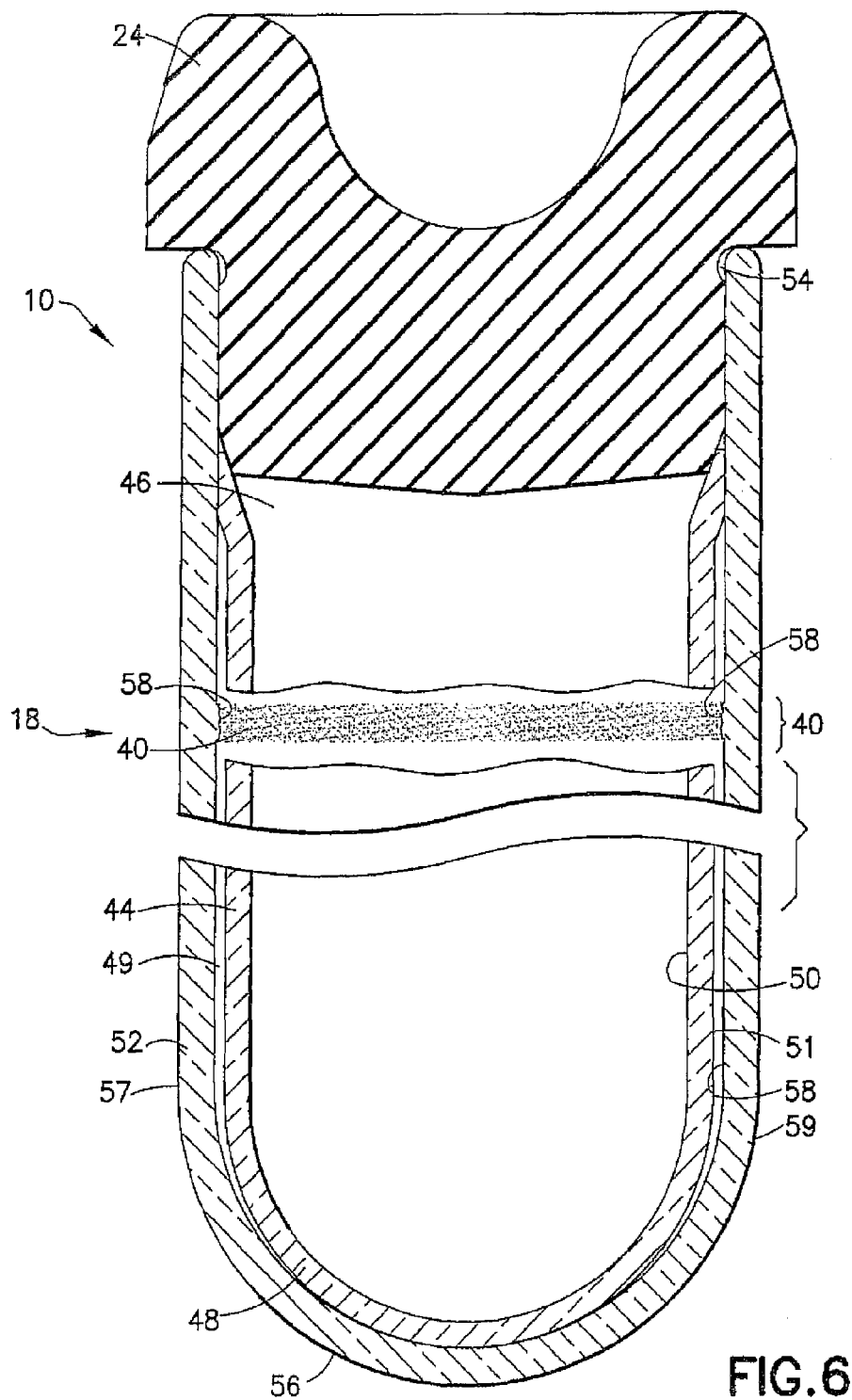
FIG. 6 shows a cross-sectional view of the thin line fill-line of FIG. 3 formed on an inner surface of a second tube according to the first embodiment of the invention.

According to a first embodiment of the invention, as shown in FIGS. 4-6, the fill-line indicator 18 can be formed on an inner surface 58 of the second or outer tubular member 52. FIG. 4 shows the fill-line indicator as a wide band indicator 26, according to a first aspect of the invention, wherein the indicator 26 is integrally formed with the inner surface 58 of the second tubular member 52 having a first predetermined width 28 defining a range for the expected fill volume for the container. FIG. 5 shows the fill-line indicator as an upper line 34 and a lower line 36, according to a second aspect of the invention, wherein these lines are integrally formed with the inner surface 58 of the second tubular member to define a range of volume 38 indicating the expected fill volume of the container 10. FIG. 6 shows the fill-line indicator as a single thin line 40, according to a third aspect of the invention wherein this line 40 is positioned on an inner surface 58 of the second tubular member 52. This single thin line 40 has a second predetermined width 42 which indicates the minimum expected fill-line for the container. As discussed in detail above, it is preferable to place this fill-line indicator on an inner surface of a tube when injection molding, as processing and removal of the molded tube having the indicator thereon is easier. Also, it is preferable to place the fill-line indicator on the outer tube when using, for example, an outer tube formed from polyethylene terephthalate, as the opacity of the fill-line provides a greater contrast with this type of material, than with the inner tube such as when such tube is formed from a polypropylene material.

It is further contemplated that such tube-in-tube container configurations may further include an outer roughened or textured surface on the inner tube to permit air to escape from the space between the containers during assembly of the inner tube within the outer tube, such as the enlarged textured top portion shown and described in the above-mentioned and incorporated U.S. Pat. No. 6,910,597. Such a roughened or textured surface at the enlarged top portion of the inner tube is separate and distinct from the textured surface representing the fill-line indicator such as fill-line indicators 26, 34, 36, 40, which also represents a roughened or textured surface, but is spaced from the top portion of the inner tube and is directly tied to the fill volume of the container, and not intended to function as an assembly feature for escape of air. The location of the indicator is also positioned with respect to the desired draw volume (of blood) and the amount of reagent, wherein the amount of reagent is chosen for the specific draw volume, and the location of the fill-line indicator 18 correlates to the amount of draw volume and reagent.

Figure 7:
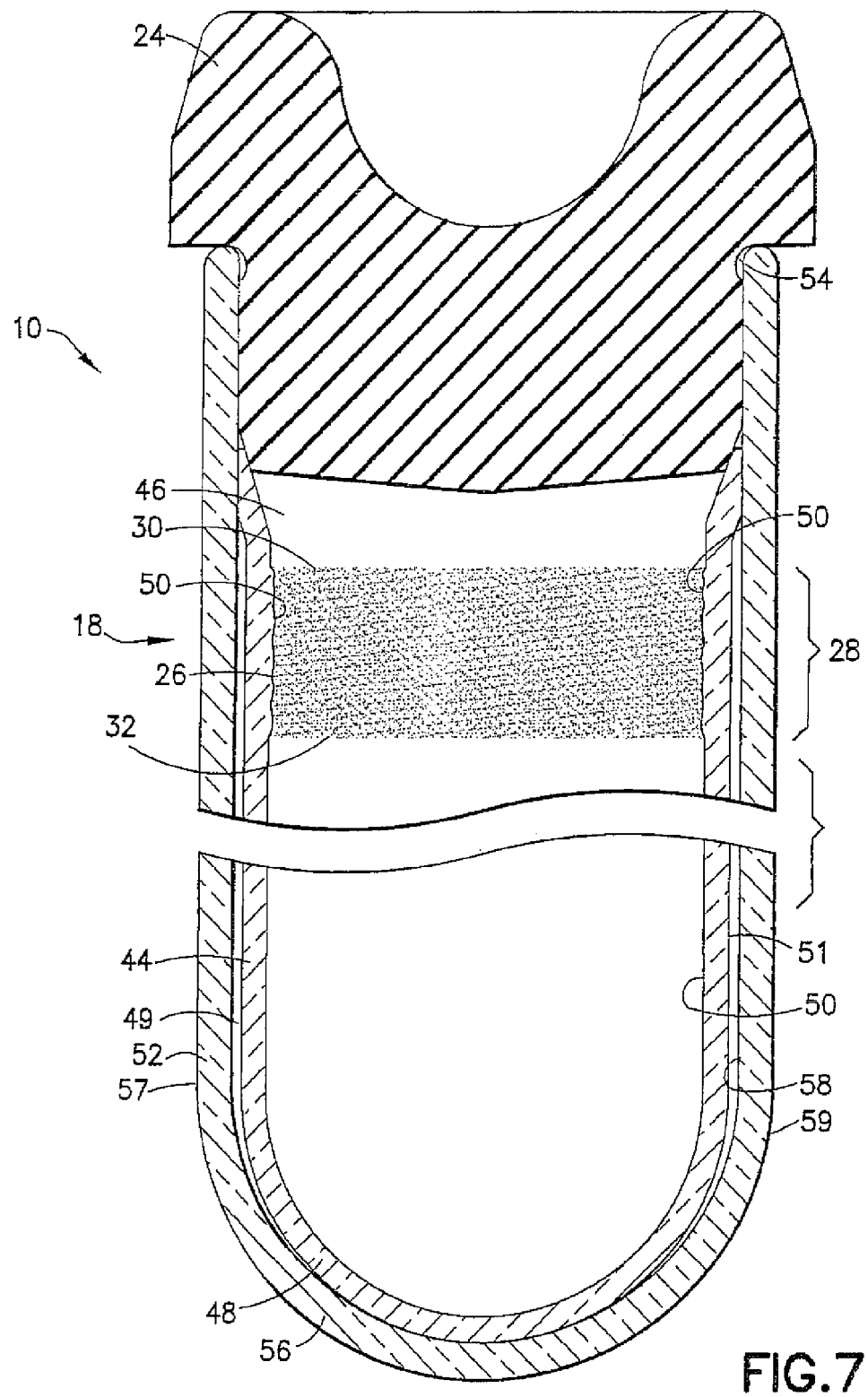
FIG. 7 shows a cross-sectional view of the wide band fill-line of FIG. 1 formed on an inner surface of a first tube according to a second embodiment of the invention.
Figure 8:
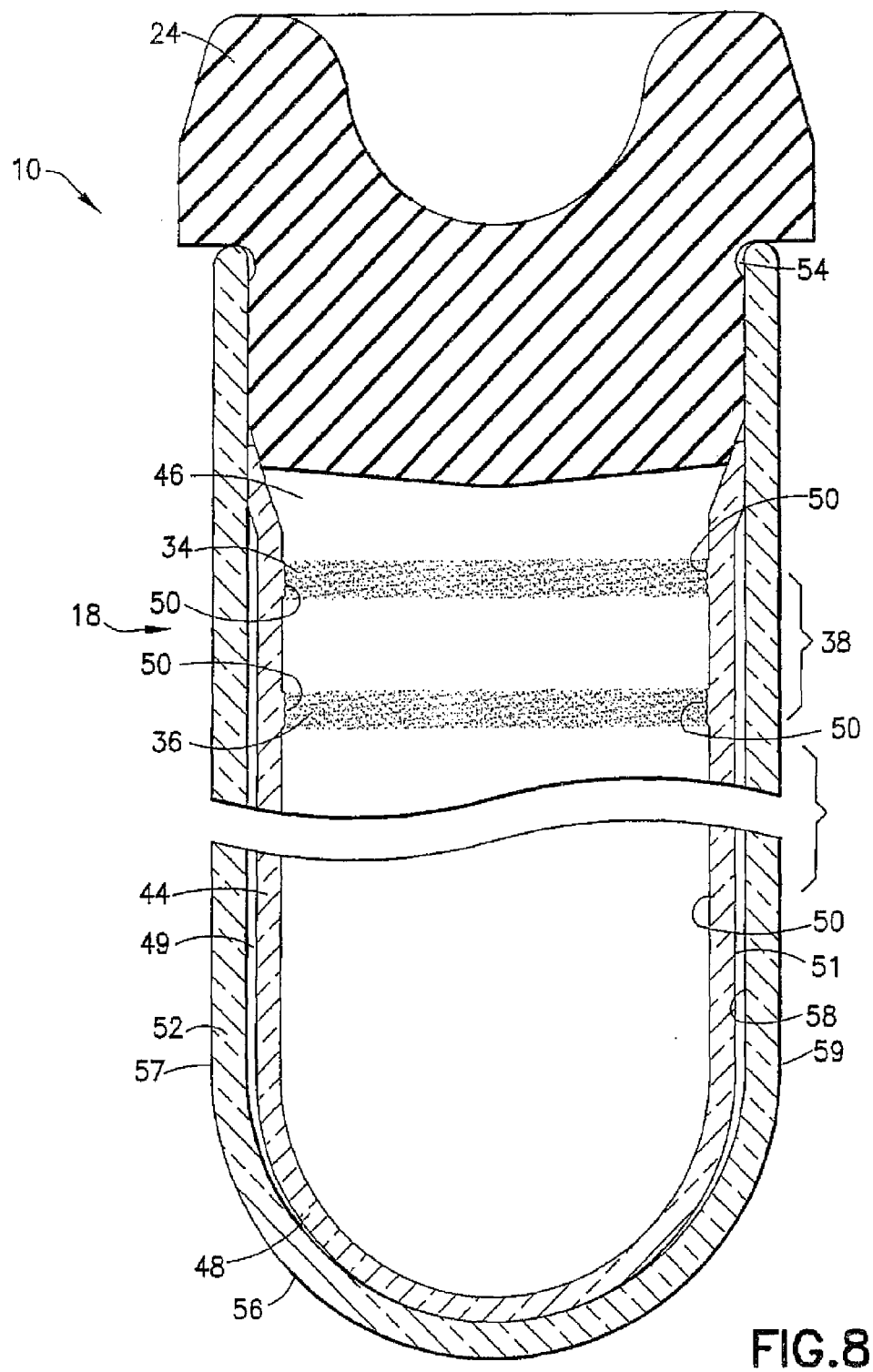
FIG. 8 shows a cross-sectional view of the pair of fill-line indicators of FIG. 2 formed on an inner surface of a first tube according to the second embodiment of the invention.
Figure 9:
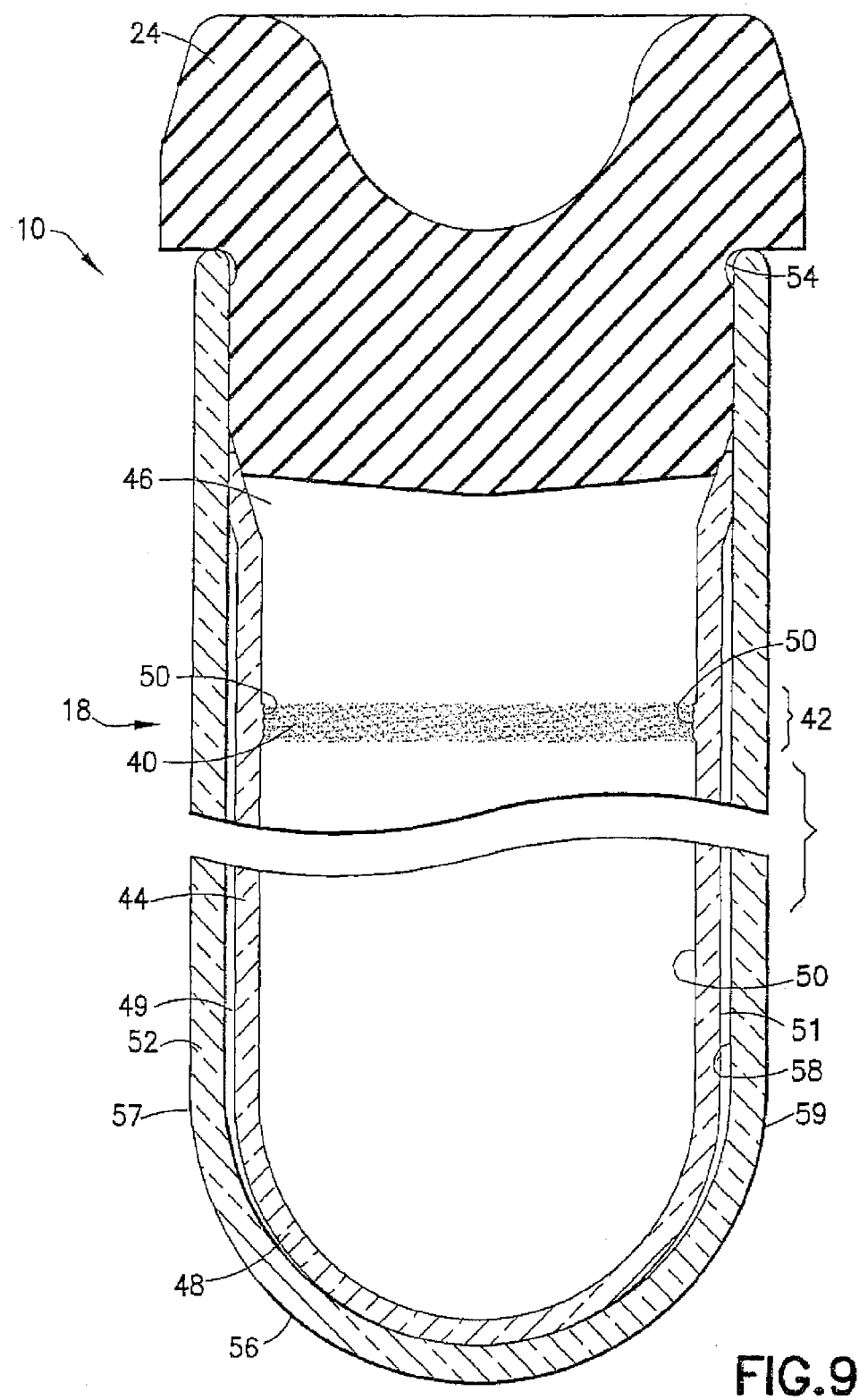
FIG. 9 shows a cross-sectional view of the thin line fill-line of FIG. 3 formed on an inner surface of a first tube according to the second embodiment of the invention.

According to a second embodiment of the invention, as shown in FIGS. 7-9, the fill-line indicator 18 can be formed on an inner surface 50 of the first or inner tubular member 44. FIG. 7 shows the fill-line indicator as a wide band indicator 26, according to a first aspect of the invention, wherein the indicator 26 is integrally formed with the inner surface 50 of the first tubular member 44 having a first predetermined width 28 defining a range for the expected fill volume for the container. FIG. 8 shows the fill-line indicator as an upper line 34 and a lower line 36, according to a second aspect of the invention, wherein these lines are integrally formed with the inner surface 50 of the first tubular member 44 to define a range of volume 38 indicating the expected fill volume of the container 10. FIG. 9 shows the fill-line indicator as a single thin line 40, according to a third aspect of the invention wherein the line is positioned integral with inner surface 50 of the first tubular member 44. This single thin line 40 has a second predetermined width 42 which indicates the minimum expected fill-line for the container.

Figure 10:
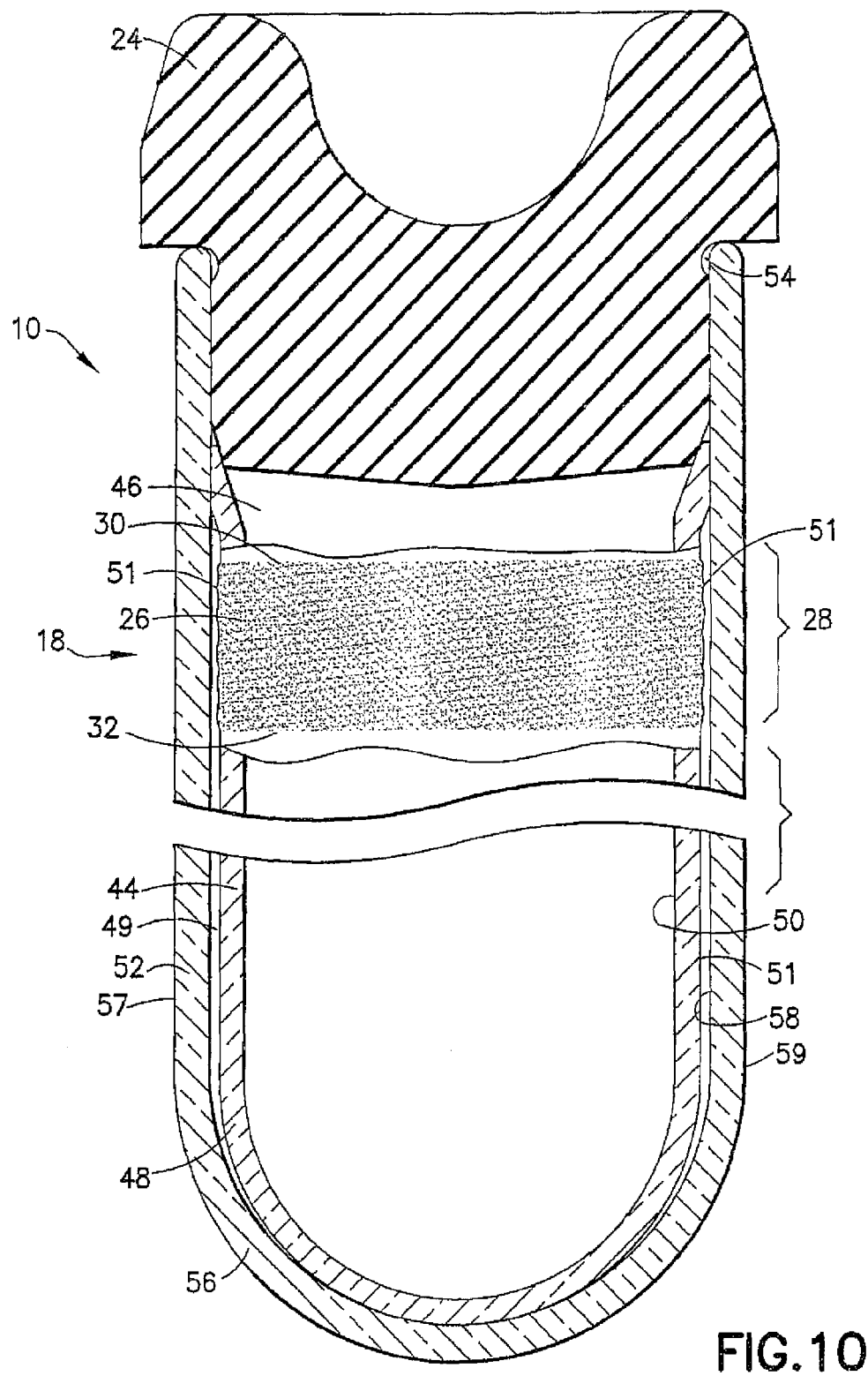
FIG. 10 shows a cross-sectional view of the wide band fill-line of FIG. 1 formed on an outer surface of a first tube according to a third embodiment of the invention.
Figure 11:
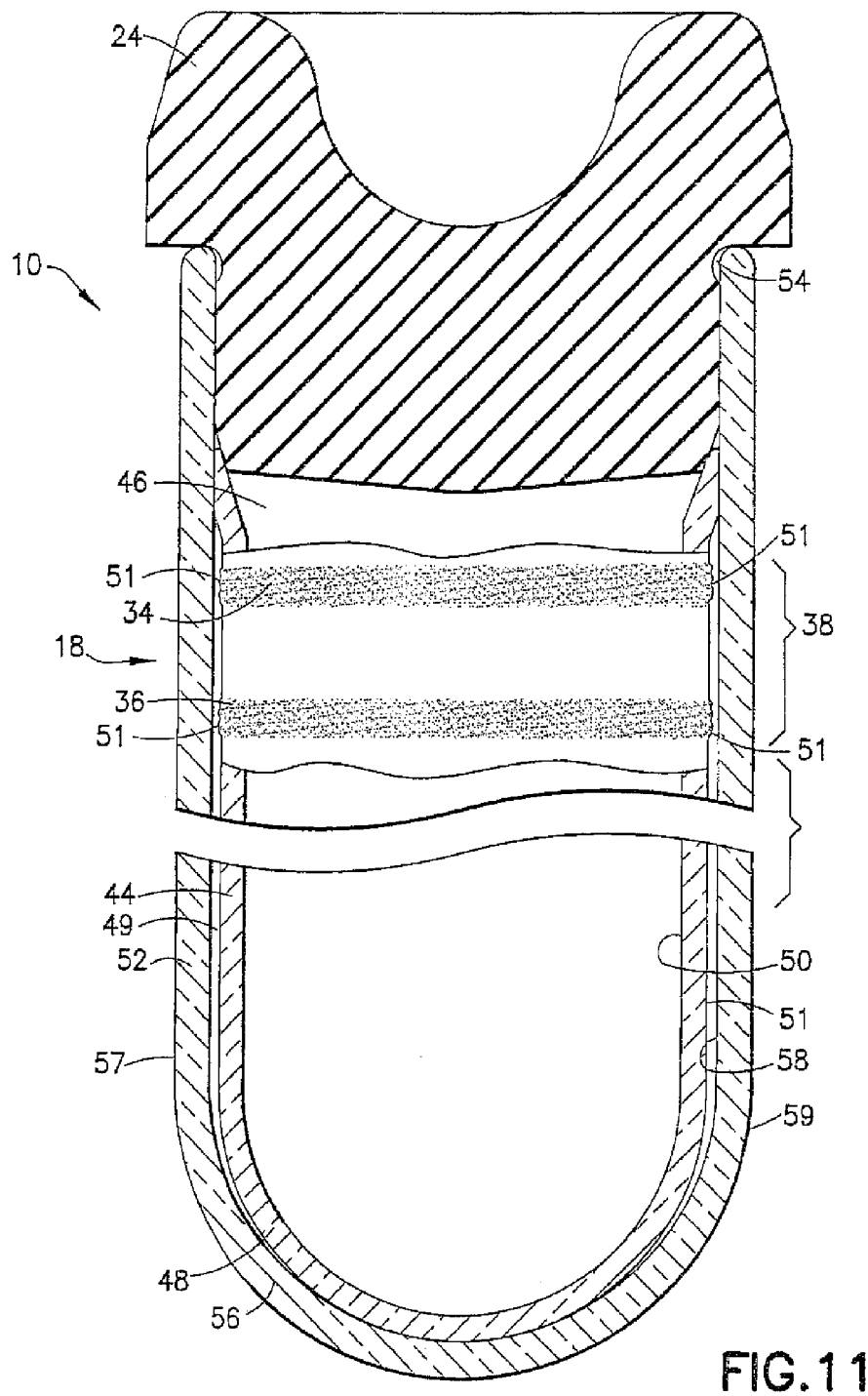
FIG. 11 shows a cross-sectional view of the pair of fill-line indicators of FIG. 2 formed on an outer surface of a first tube according to the third embodiment of the invention.
Figure 12:
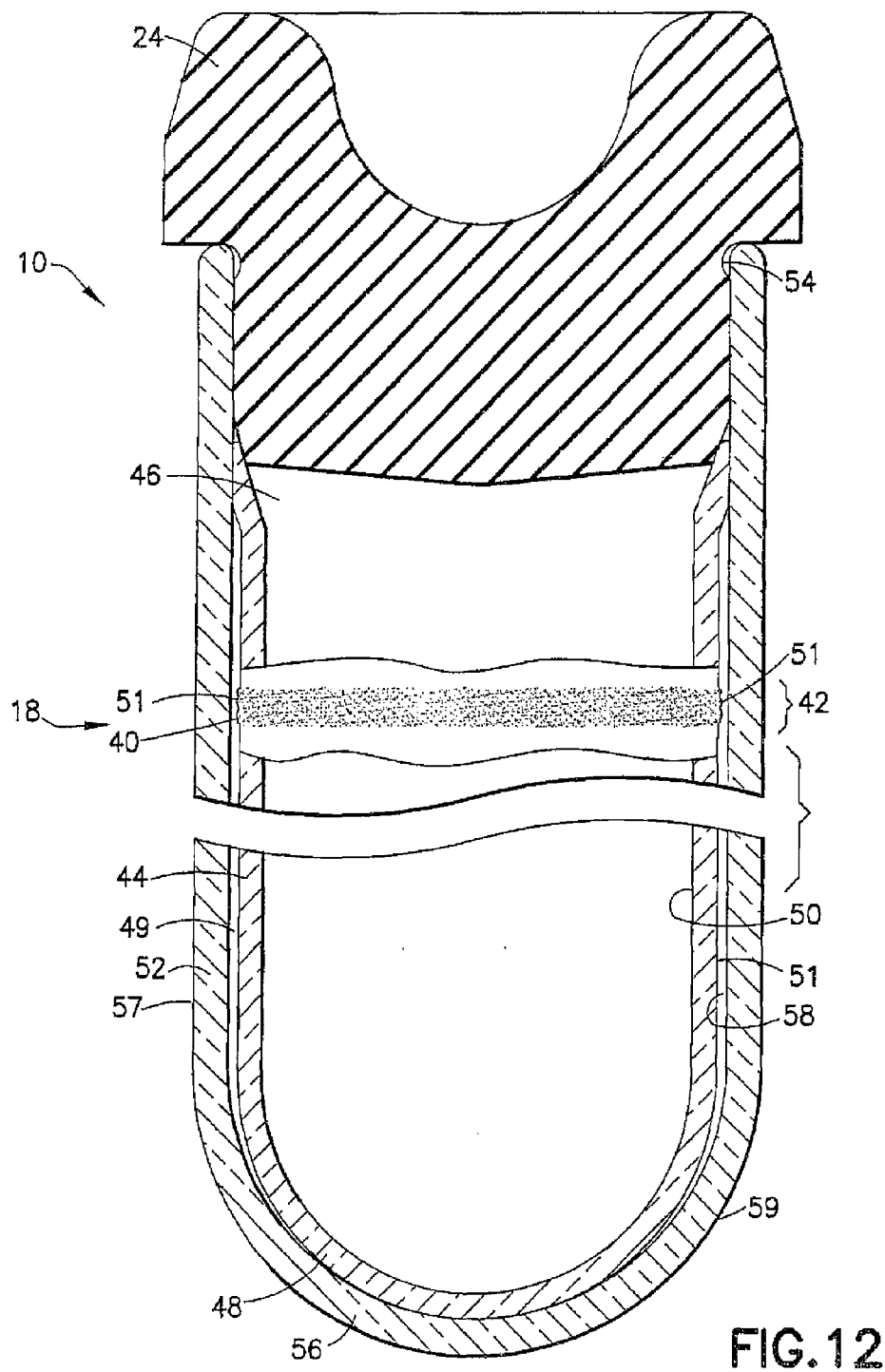
FIG. 12 shows a cross-sectional view of the thin line fill-line of FIG. 3 formed on an outer surface of a first tube according to the third embodiment of the invention.

According to a third embodiment of the invention, as shown in FIGS. 10-12, the fill-line indicator 18 can be formed on an outer surface 51 of the first or inner tubular member 44. FIG. 10 shows the fill-line indicator as a wide band indicator 26, according to a first aspect of the invention, wherein the indicator 26 is integrally formed with the outer surface 51 of the first tubular member 44 having a first predetermined width 28 defining a range for the expected fill volume for the container. FIG. 11 shows the fill-line indicator as an upper line 34 and a lower line 36, according to a second aspect of the invention, wherein these lines are integrally formed with the outer surface 51 of the first tubular member 44 to define a range of volume 38 indicating the expected fill volume of the container 10. FIG. 12 shows the fill-line indicator as a single thin line 40, according to a third aspect of the invention wherein the line is positioned integral with outer surface 50 of the first tubular member 44. This single thin line 40 has a second predetermined width 42 which indicates the minimum expected fill-line for the container.

Figure 13:
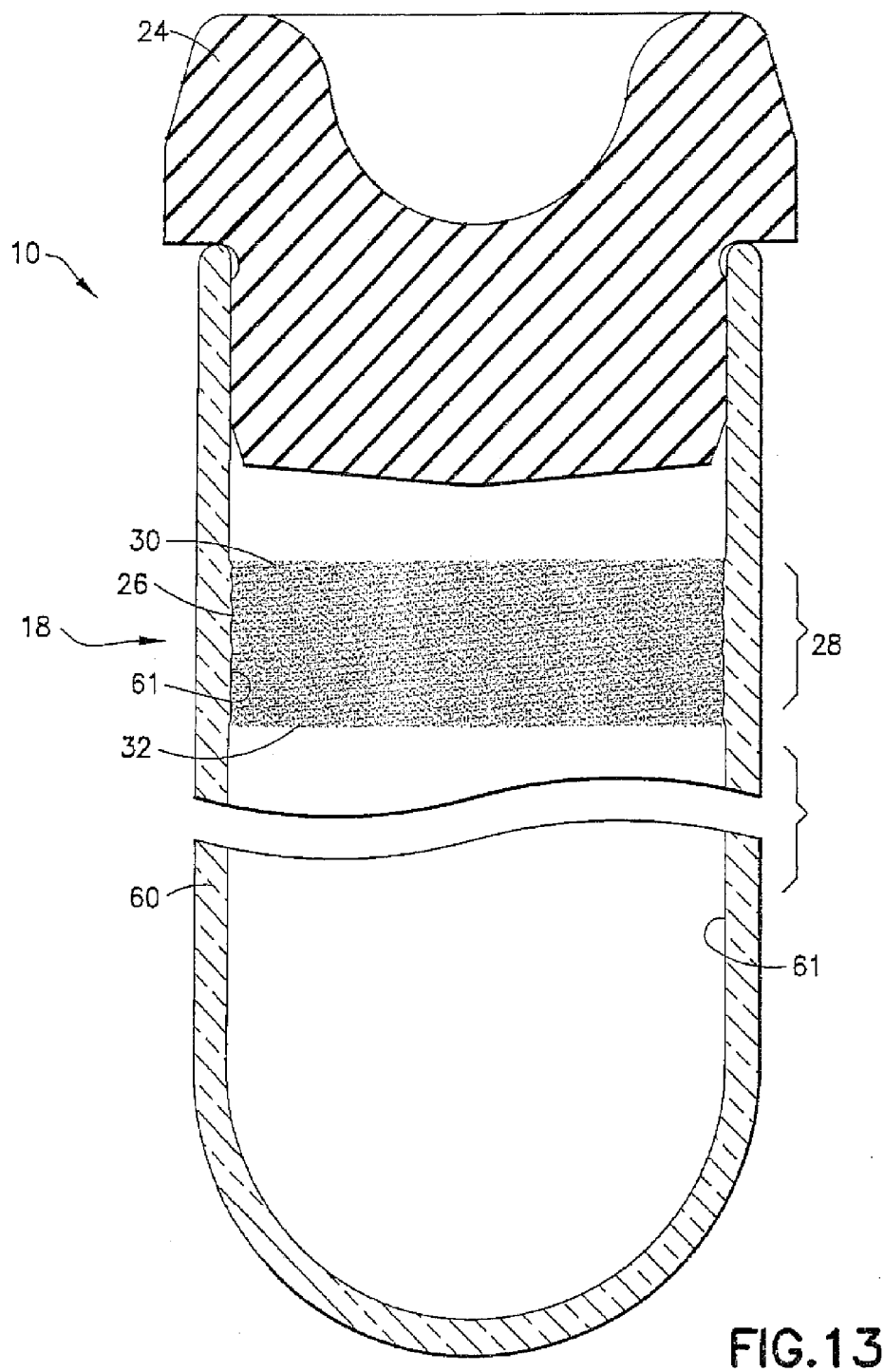
FIG. 13 shows a cross-sectional view of the wide band fill-line of FIG. 1 formed on an inner surface of a single tube according to a fourth embodiment of the invention.
Figure 14:
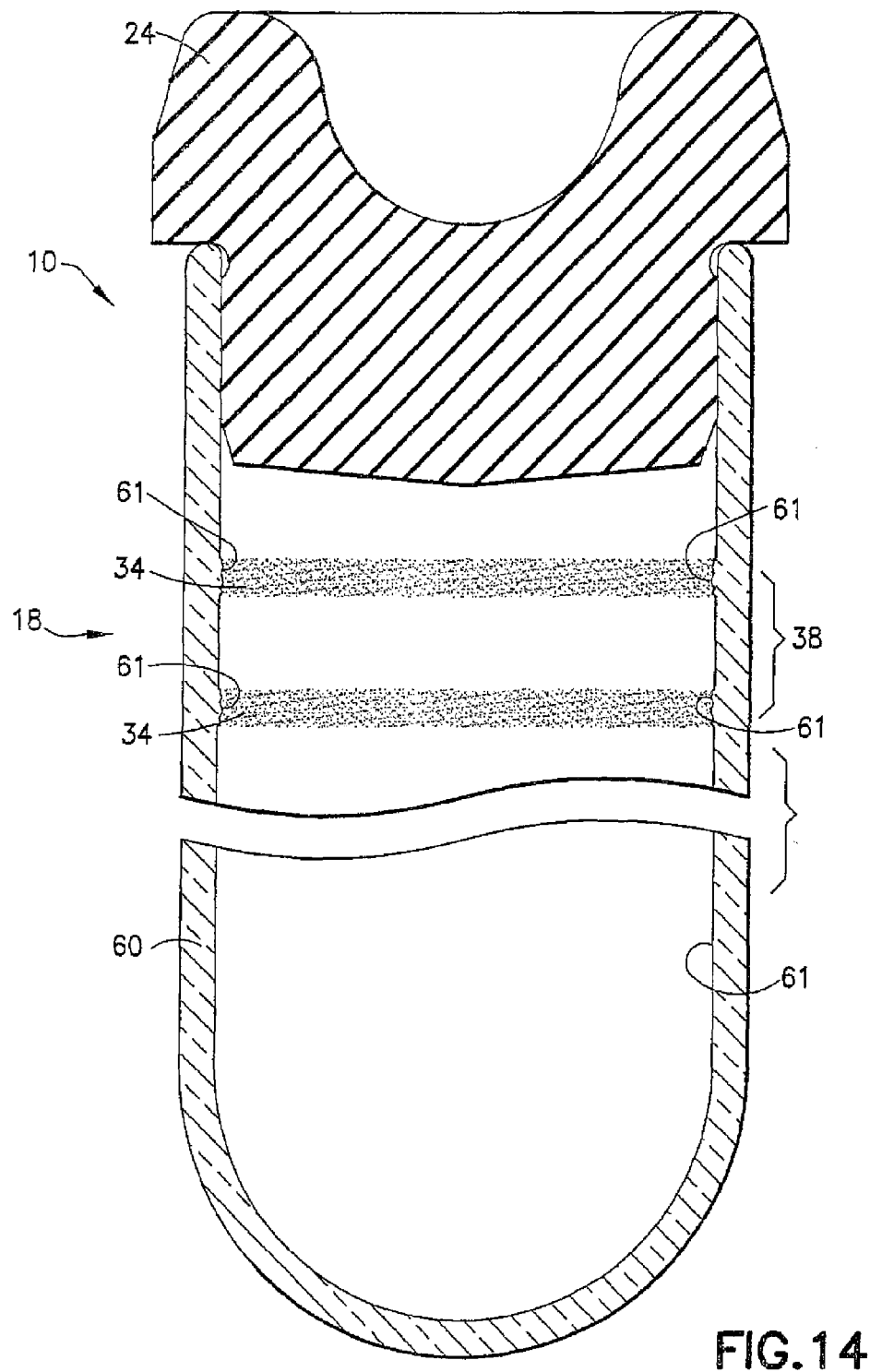
FIG. 14 shows a cross-sectional view of the pair of fill-line indicators of FIG. 2 formed on an inner surface of a single tube according to the fourth embodiment of the invention.
Figure 15:
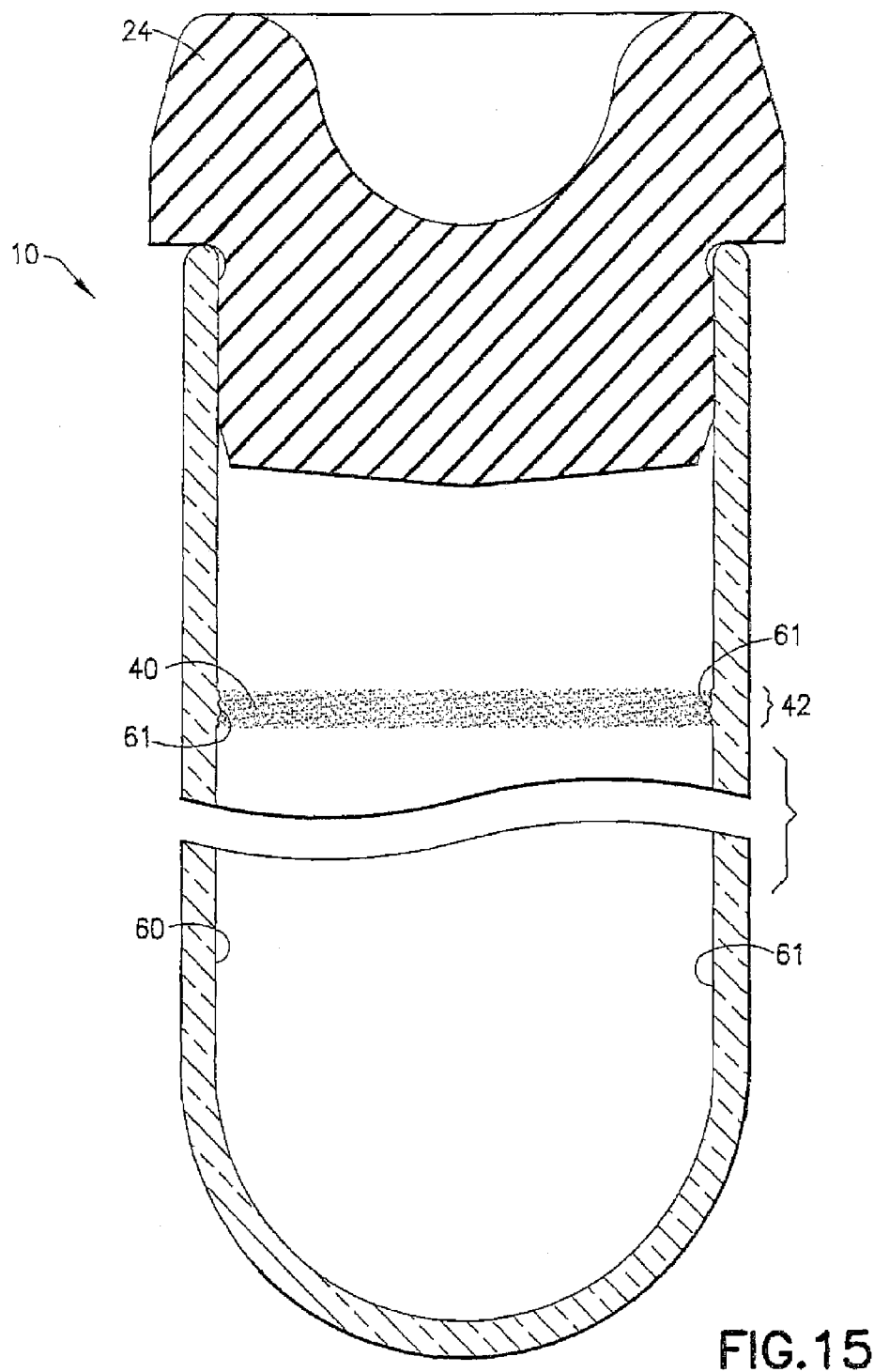
FIG. 15 shows a cross-sectional view of the thin line fill-line of FIG. 3 formed on an inner surface of a single tube according to the fourth embodiment of the invention.

According to a fourth embodiment of the invention, and as shown in FIGS. 13-15 of the invention, the fill-line indicator 18 of the present invention can be used with other types of containers besides the tube-in-tube configurations. For example, the fill-line indicator 18 can be used with a single tubular member 60. As shown in FIG. 13, the fill-line indicator 18 can be formed on an inner surface 61 of the tubular member 60 as a wide band indicator 26, according to a first aspect of the invention, wherein the indicator 26 is integrally formed with the inner surface 61 of the tubular member 60 and the indicator has a first predetermined width 28 defining a range for the expected fill volume for the container. FIG. 14 shows the fill-line indicator as an upper line 34 and a lower line 36, according to a second aspect of the invention, wherein these lines are integrally formed with the inner surface 61 of the tubular member 60 to define a range of volume 38 indicating the expected fill volume of the container 10. FIG. 15 shows the fill-line indicator as a single thin line 40, according to a third aspect of the invention wherein this line 40 is positioned on an inner surface 61 of the tubular member 60. This single thin line 40 has a second predetermined width 42 which indicates the minimum expected fill-line for the container.

Figure 16:
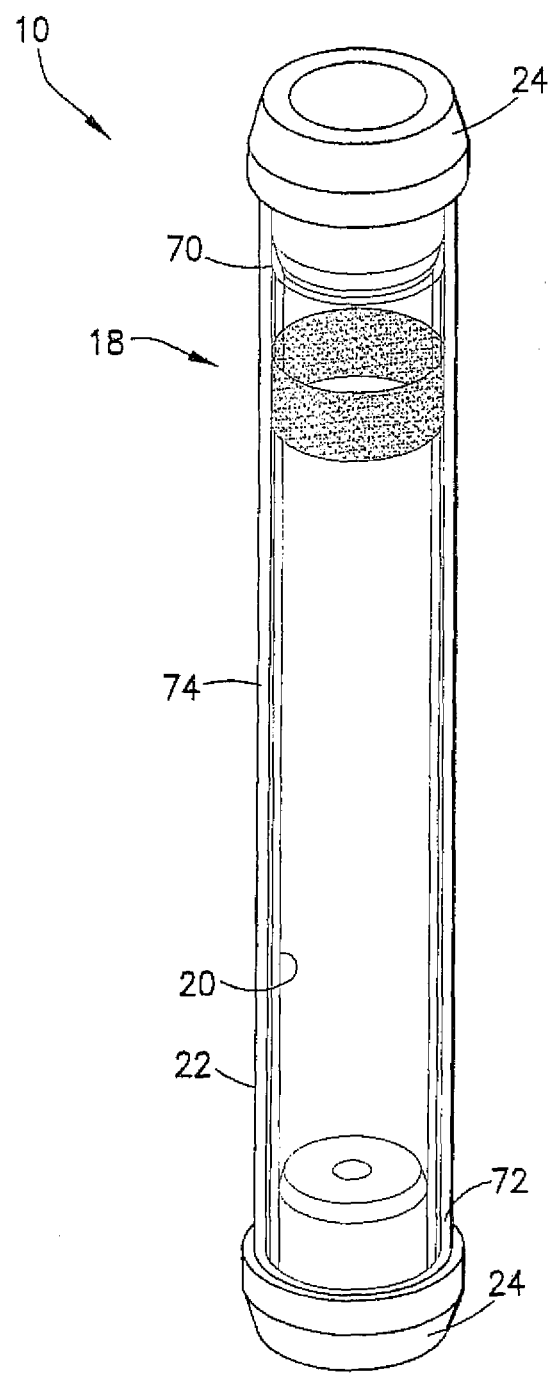
FIG. 16 shows a perspective view of a double-open ended tube according to another embodiment of the invention.

Although the previously discussed embodiments have been directed to closed end tubular containers, the use of a fill-line indicator 18 may be used on double-ended open tubes, such as shown in FIG. 16. In this embodiment, the container assembly comprises a tubular member having a first end 70, a second end 72, and a sidewall 74 extending circumferentially between the first end 70 and the second end 72. The fill-line indicator 18 corresponds to at least a minimum expected fill volume of the collection container. The first end 70 and second end 72 may be closed by closures 24. Although FIG. 16 shows the fill-line indicator 26, according to a first aspect of the invention, the fill-line indicator 18 may comprises any of the fill-line indicator designs 26, 32, 34, 40 according to the first, second, or third aspects of the invention.

While specific embodiments of the invention have been described in detail, it will be appreciated by those skilled in the art that various modifications and alternatives to those details could be developed in light of the overall teachings of the disclosure. For example, while the fill-lines are described above such that they are parallel with the circumference of the open end of the container or container assembly, the fill-line may be disposed on the container or assembly at an angle such that the volume of a sample can be recognized when the container or assembly is at an angle. In addition, while the fill-lines described above are positioned such that it surrounds the entire circumference of the container or assembly, in some embodiments, the fill-line(s) may surround only a portion of the container or assembly and/or may be situated in segments (e.g., broken line(s)). Further, it should be noted that the fill-line(s) situated on a container assembly may be situated on the outer tube, inner tube, or both tubes. Moreover, while the embodiments describe the inclusion of fill-line(s) on a container or assembly in the form of one more tubes, additional types of container structures (such as collection bags) may employ one or more of the described fill-line features.

The invention claimed is:

1. A specimen collection container assembly comprising:
   a first tubular member having a first opening, a first closed bottom, and a first sidewall extending circumferentially between said first opening and said first closed bottom, said first tubular member capable of receiving a specimen sample therein;
   a second tubular member having a second opening, a second closed bottom, and a second sidewall extending circumferentially between said second opening and said second closed bottom, said first tubular member non-removably engaged with said second tubular member; and
   a fill-line indicator integrally formed with an inner surface of at least one of said first and second sidewall, said fill-line indicator corresponding to at least a minimum expected fill volume of the collection container,
   wherein said fill-line indicator is integrally formed with said inner surface of said second sidewall, wherein the first tubular member defines an internal volume, wherein the fill-line indicator corresponds to at least a minimum expected fill volume of the internal volume defined by the first tubular member, wherein said fill-line indicator comprises a roughened surface that defines an array of peaks and valleys, and wherein the remainder of the inner surface of the second sidewall comprises a highly polished transparent surface, and wherein said fill-line indicator provides an enlarging effect to the specimen sample when a meniscus of a fluid level of the specimen sample is at the fill-line indicator, providing an apparent indication of reaching such level of containment.

2. The container assembly of claim 1 wherein said fill-line indicator is a textured surface capable of diffusing light.

3. The container assembly of claim 1 wherein the fill-line indicator comprises a single wide band extending at least partially circumferentially about a portion of said second sidewall, said single band having a first predetermined width defined by an upper boundary and a lower boundary, said upper boundary defining a maximum expected fill volume, said lower boundary defining a minimum expected fill volume.

4. The container assembly of claim 1 wherein the fill-line indicator comprises an upper line and a lower line extending at least partially circumferentially about a portion of said second sidewall and spaced a predetermined distance from each other, said upper line defining a maximum expected fill volume and said lower line defining a minimum expected fill volume.

5. The container assembly of claim 1 wherein the fill-line indicator comprises a line extending at least partially circumferentially about a portion of said second sidewall, said single line having a second predetermined width corresponding to a minimum volume of the expected fill volume of said collection container.

6. The container assembly of claim 1 wherein said first tubular member is formed from a moisture barrier material and said second tubular member is formed from a vapor barrier material.

7. The container assembly of claim 6 wherein said first tubular member comprises polypropylene and said second tubular member comprises polyethylene terephthalate.

8. The container assembly of claim 1 wherein the container assembly further includes a pierceable closure wherein the pressure of the internal volume is reduced with respect to atmosphere.

9. The container assembly of claim 8 wherein the fill-line indicator is positioned on said second sidewall so as to indicate at least a minimum expected fill volume of the specimen sample according to the reduced pressure of the internal volume of said container.

10. The container assembly of claim 8 wherein the fill-line indicator is positioned so as to indicate at least a minimum expected fill volume of the specimen sample in combination with a pre-filled reagent located within said container in accordance with the reduced pressure of the internal volume of said container.

11. A biological specimen collection container assembly comprising:
    a first tubular member having a first opening, a first closed bottom, and a first sidewall extending circumferentially between said first opening and said first closed bottom, said first tubular member capable of receiving a specimen sample therein;
    a second tubular member having a second opening, a second closed bottom, and a second sidewall extending circumferentially between said second opening and said second closed bottom, said second sidewall having an inner and outer surface and a fill-line indicator integrally formed with an inner surface of said second sidewall, said fill-line indicator corresponding to at least a minimum expected fill volume of the collection, said first tubular member non-removably engaged with said second tubular member,
    wherein the first tubular member defines an internal volume, wherein the fill-line indicator corresponds to at least a minimum expected fill volume of the internal volume defined by the first tubular member, wherein said fill-line indicator comprises a roughened surface that defines an array of peaks and valleys, and wherein the remainder of the inner surface of the second sidewall comprises a highly polished transparent surface, and wherein said fill-line indicator provides an enlarging effect to the specimen sample when a meniscus of a fluid level of the specimen sample is at the fill-line indicator, providing an apparent indication of reaching such level of containment.

12. The container assembly of claim 11 wherein the fill-line indicator comprises a line extending at least partially circumferentially about a portion of said inner surface of said second sidewall, said line having a second predetermined width corresponding to a minimum volume of the expected fill volume of said collection container.

13. The container assembly of claim 11 wherein said fill-line indicator is a textured surface capable of diffusing light.

14. The container assembly of claim 11 wherein said minimum expected fill volume corresponds with one of a biological specimen sample to be received within said container or a biological specimen sample and a reagent present within the container.

15. The container assembly of claim 11 wherein the container assembly further includes a pierceable closure wherein the pressure of the internal volume is reduced with respect to atmosphere.

16. A method of making a specimen collection container comprising:
    molding a first tubular member having a first opening, a first closed bottom, and a first sidewall extending circumferentially between said first opening and said first closed bottom, said first tubular member having a predetermined volume for receiving a specimen sample therein;

molding a second tubular member having a second opening, a second closed bottom, and a second sidewall extending circumferentially between said second opening and said second closed bottom;

providing a fill-line indicator integrally formed with an inner surface of at least one of said first and second sidewall, said fill-line indicator corresponding to at least a minimum expected fill volume of the collection container; and non-removably engaging said first tubular member with said second tubular member, wherein at least said second tubular member is formed by an injection molding process including a core member and said fill-line indicator is formed on an inner surface of said second sidewall by providing a roughened surface at least partially circumventing a perimeter of said core member, wherein said fill-line indicator comprises a roughened surface that defines an array of peaks and valleys, and wherein the remainder of the inner surface of the second sidewall comprises a highly polished transparent surface, and wherein said fill-line indicator provides an enlarging effect to the specimen sample when a meniscus of a fluid level of the specimen sample is at the fill-line indicator, providing an apparent indication of reaching such level of containment.

17. The method of claim 16 wherein the fill-line indicator comprises a single wide band extending at least partially circumferentially about a portion of said second sidewall, said band having a first predetermined width defined by an upper boundary and a lower boundary, said upper boundary defining a maximum expected fill volume, said lower boundary defining a minimum expected fill volume.

18. The method of claim 16 wherein the fill-line indicator comprises an upper and lower line extending at least partially circumferentially about a portion of said second sidewall and spaced a predetermined distance from each other, said upper fill-line defining a maximum expected fill volume and said lower line defining a minimum expected fill volume.

19. The method of claim 16 wherein the fill-line indicator comprises a line extending at least partially circumferentially about a portion of-said second sidewall, said line having a first predetermined width corresponding to a minimum expected volume of the expected fill volume of said collection container.

* * * * *